(12) United States Patent
Sakai et al.

(10) Patent No.: US 7,846,902 B2
(45) Date of Patent: Dec. 7, 2010

(54) DIPEPTIDE-COMPRISING COMPOSITION FOR ORAL ADMINISTRATION

(75) Inventors: Yasushi Sakai, Ibaraki (JP); Masao Kimura, Ibaraki (JP); Shun Kayahashi, Ibaraki (JP); Toshikazu Kamiya, Ibaraki (JP); Shin-ichi Hashimoto, Yamaguchi (JP); Hideo Kawabe, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 12/066,849

(22) PCT Filed: Sep. 20, 2006

(86) PCT No.: PCT/JP2006/318584

§ 371 (c)(1),
(2), (4) Date: Jul. 15, 2008

(87) PCT Pub. No.: WO2007/034807

PCT Pub. Date: Mar. 29, 2007

(65) Prior Publication Data

US 2008/0305151 A1    Dec. 11, 2008

(30) Foreign Application Priority Data

Sep. 20, 2005  (JP) .............................. 2005-272670

(51) Int. Cl.
*A61K 38/05* (2006.01)
*A61K 9/00* (2006.01)

(52) U.S. Cl. ...................... 514/21.91; 514/1.1; 424/439

(58) Field of Classification Search .................. None
See application file for complete search history.

(56) References Cited

U.S. PATENT DOCUMENTS

| | | | |
|---|---|---|---|
| 4,340,592 A | 7/1982 | Adibi | |
| 5,034,377 A | 7/1991 | Adibi et al. | |
| 5,036,052 A | 7/1991 | Ozeki et al. | |
| 2003/0099689 A1 | 5/2003 | Dabrowski et al. | |
| 2004/0014678 A1* | 1/2004 | Favit et al. | ............ 514/19 |
| 2004/0171106 A1 | 9/2004 | Hashimoto et al. | |

FOREIGN PATENT DOCUMENTS

| | | |
|---|---|---|
| EP | 0 182 356 | 5/1986 |
| JP | 56-140923 | 11/1981 |
| JP | 61-247354 | 11/1986 |
| JP | 62-151156 | 7/1987 |
| JP | 02-022232 | 1/1990 |
| JP | 2-157230 | 6/1990 |
| JP | 03-127737 | 5/1991 |
| JP | 2529603 | 6/1996 |
| JP | 10-287562 | 10/1998 |
| JP | 2002-253171 | 9/2002 |
| JP | 2005-336078 | 12/2005 |
| WO | 2004-058960 | 7/2004 |
| WO | 2004/078780 | 9/2004 |

OTHER PUBLICATIONS

Synge, et al., "A Further Study of Hydrolysates of Gramicidin", The Biochemical Journal, vol. 44, No. 5 (1949) 542-48.

* cited by examiner

*Primary Examiner*—Julie Ha
(74) *Attorney, Agent, or Firm*—Fitzpatrick, Cella, Harper & Scinto

(57) ABSTRACT

A composition for oral administration is provided, which includes at least one dipeptide represented by the formula:

$$X-Y$$

(wherein X represents alanyl, and Y represents valine, leucine or isoleucine), with an object of providing a composition for oral administration which is excellent in nutrition, pharmacological effect and gustation, or providing a composition for oral administration which is excellent in processing characteristics such as solubility and tabletting property.

19 Claims, No Drawings

DIPEPTIDE-COMPRISING COMPOSITION FOR ORAL ADMINISTRATION

TECHNICAL FIELD

The present invention relates to a composition for oral administration comprising at least one selected from valine, leucine and isoleucine as an amino acid or a constituent amino acid. In the present description, the "amino acid" denotes a monomer amino acid, while the "constituent amino acid" denotes amino acids in a protein or a peptide.

BACKGROUND ART

Valine, leucine and isoleucine are known as branched chain amino acids (BCAA), and have long been used as the components for nutritious foods, nutritious compositions for infusions, and the like as essential amino acids. The composition comprising valine, leucine and isoleucine as active components is also widely used for nutritious supplements for sports or the like since it has physiological effects such as reduction of muscle fatigue. Furthermore, the composition comprising valine, leucine and isoleucine as active components is known as drug product for treatment of hepatic diseases and as medical food used for treatment of tardive dyskinesia.

The form for oral intake of BCAA includes a beverage, a granule, a tablet and the like. Some modification is necessary in the taste in these beverage, granule and tablet since BCAA has a peculiar bitter taste. In addition, production of a tablet comprising BCAA is difficult because BCAA is apt to adhere to a punch and die of a compression molding machine and causes a compression molding problem such as capping and sticking, so there was a need to prevent the compression molding problem.

A nutritious composition for infusions which comprises dipeptide having leucine at the C-terminal is disclosed in PATENT DOCUMENT 1, a nutritious composition for infusions which comprises dipeptide having leucine at the C-terminal, valine and isoleucine is disclosed in PATENT DOCUMENT 2, and a nutritious composition for infusions which comprises dipeptide having α-aspartyl at the N-terminal and valine, leucine or isoleucine at the C-terminal is disclosed in PATENT DOCUMENT 3. A liquid nutritious composition which comprises dipeptide having glycyl at the N-terminal and valine, leucine or isoleucine at the C-terminal is disclosed in PATENT DOCUMENT 4.

A method for producing dipeptide having leucine, isoleucine or valine at the C-terminal by using a microorganism is also disclosed in Patent Document 5.

PATENT DOCUMENT 1 JP-A-2-22232
PATENT DOCUMENT 2 JP-A-3-127737
PATENT DOCUMENT 3 JP-A-62-151156
PATENT DOCUMENT 4 JP-A-61-247354
PATENT DOCUMENT 5 WO 2004/58960 Pamphlet

DISCLOSURE OF THE INVENTION

Problems to be Solved by the Invention

An object of the present invention is to provide a composition for oral administration which is excellent in nutrition, pharmacological effect and gustation, and comprises at least one selected from valine, leucine and isoleucine as an amino acid or a constituent amino acid, and to provide a composition for oral administration which is excellent in processing characteristics such as solubility and tableting property, and comprises at least one selected from valine, leucine and isoleucine as an amino acid or a constituent amino acid.

Means for Solving the Problems

The present invention relates to the following (1) to (9).

(1) A composition for oral administration comprising at least one kind of dipeptide represented by the formula:

$$X\text{---}Y$$

wherein X represents alanyl, glycyl, arginyl, seryl, α-aspartyl or α-glutamyl, and Y represents valine, leucine or isoleucine.

(2) The composition according to (1), wherein X is alanyl, arginyl or α-glutamyl.

(3) The composition according to (1) or (2), wherein the composition is a nutritious food or a drug product for oral administration.

(4) The composition according to (3), wherein the composition is a tablet or a granule.

(5) The composition according to (3), wherein the composition is a beverage.

(6) The composition according to any one of (1) to (5), comprising at least one kind of dipeptide wherein Y is valine, at least one kind of dipeptide wherein Y is leucine, and at least one kind of dipeptide wherein Y is isoleucine.

(7) The composition according to (6), further comprising at least one kind of amino acid selected from valine, leucine and isoleucine.

(8) The composition according to any one of (1) to (5), further comprising at least one kind of amino acid selected from valine, leucine and isoleucine and combining the said amino acid together with the constituent amino acid of the above-mentioned dipeptide so as to comprise valine, leucine and isoleucine.

(9) The composition according to any one of (6) to (8), wherein the total leucine content in the composition is 1 to 3 times the total valine content or total isoleucine content.

EFFECTS OF THE INVENTION

The present invention provides a composition for oral administration which is excellent in nutrition, pharmacological effect and gustation, and comprises at least one kind of dipeptide comprising valine, leucine or isoleucine. The present invention also provides a composition for oral administration which has improved solubility and tableting property by modifying at least one selected from valine, leucine and isoleucine into dipeptide, and comprises at least one kind of the dipeptide comprising valine, leucine or isoleucine.

BEST MODE FOR CARRYING OUT THE INVENTION

The composition of the present invention comprises at least one kind of dipeptide (hereinafter called dipeptide (1)) represented by the formula:

$$X-Y \qquad (I)$$

(wherein X represents alanyl, glycyl, arginyl, seryl, α-aspartyl or α-glutamyl, and Y represents valine, leucine or isoleucine).

Examples of dipeptide which belongs to the dipeptide (1) of the present invention include alanyl-valine, alanyl-leucine, alanyl-isoleucine, glycyl-valine, glycyl-leucine, glycyl-isoleucine, arginyl-valine, arginyl-leucine, arginyl-isoleucine, seryl-valine, seryl-leucine, seryl-isoleucine, α-aspartyl-valine, α-aspartyl-leucine, α-aspartyl-isoleucine, α-glutamyl-valine, α-glutamyl-leucine and α-glutamyl-isoleucine. Preferred examples include alanyl-valine, alanyl-leucine, alanyl-isoleucine, arginyl-valine, arginyl-leucine, arginyl-isoleucine, α-glutamyl-valine, α-glutamyl-leucine and α-glutamyl-isoleucine, and more preferred examples include alanyl-valine, alanyl-leucine and alanyl-isoleucine. The dipeptide (1) contained in the composition of the present invention may be used alone or in combination of two or more.

In addition, the dipeptide (1) of the present invention may be a salt. Examples of the salt include an organic acid salt or an inorganic acid salt such as a hydrochloride, sulfate and acetate; and a base salt such as a sodium salt and potassium salt. The dipeptide (1) of the present invention is a composition which comprises valine, leucine or isoleucine as a constituent amino acid.

The dipeptide (1) of the present invention can be prepared by any production methods. Specific examples of the method include an extraction/purification method of a naturally-derived substance obtained by hydrolysis, or the like, of a natural product or protein, a chemical synthesis method in which a peptide bond is formed between amino acids by a solid or liquid phase method, a biochemical synthesis method in which amino acids are bonded by using an enzyme or microorganism, and the like. Among them, the biochemical synthesis method described in Patent Document 5 is adequate as a synthetic method in a mass scale.

It is preferred that the composition of the present invention comprises at least one dipeptide represented by the formula wherein Y is valine, at least one dipeptide represented by the formula wherein Y is leucine, and at least one dipeptide represented by the formula wherein Y is isoleucine. Examples of the composition include a composition comprising alanyl-leucine, alanyl-isoleucine and alanyl-valine, a composition comprising glycyl-leucine, glycyl-isoleucine and glycyl-valine, a composition comprising arginyl-leucine, arginyl-isoleucine and arginyl-valine, a composition comprising seryl-leucine, seryl-isoleucine and seryl-valine, a composition comprising α-aspartyl-leucine, α-aspartyl-isoleucine and α-aspartyl-valine, a composition comprising α-glutamyl-leucine, α-glutamyl-isoleucine and α-glutamyl-valine, and the like. These compositions may comprise at least one kind of amino acid selected from valine, leucine and isoleucine, other than the dipeptide (1).

It is also preferred that the composition of the present invention comprises at least one kind of amino acid selected from valine, leucine and isoleucine, in addition to the dipeptide (1) so as to comprise valine, leucine and isoleucine together with the said amino acid constituent amino acid of dipeptide (1). Examples of the composition include a composition comprising alanyl-leucine, isoleucine and valine, a composition comprising alanyl-leucine, alanyl-isoleucine and valine, a composition comprising leucine, alanyl-isoleucine and valine, a composition comprising leucine, isoleucine and alanyl-valine, a composition comprising glycyl-leucine, isoleucine and valine, a composition comprising glycyl-leucine, glycyl-isoleucine and valine, a composition comprising leucine, glycyl-isoleucine and valine, a composition comprising leucine, isoleucine and glycyl-valine, a composition comprising arginyl-leucine, isoleucine and valine, a composition comprising arginyl-leucine, arginyl-isoleucine and valine, a composition comprising leucine, arginyl-isoleucine and valine, a composition comprising leucine, isoleucine and arginyl-valine, a composition comprising seryl-leucine, isoleucine and valine, a composition comprising seryl-leucine, seryl-isoleucine and valine, a composition comprising leucine, seryl-isoleucine and valine, a composition comprising leucine, isoleucine and seryl-valine, a composition comprising 0-aspartyl-leucine, isoleucine and valine, a composition comprising α-aspartyl-leucine, α-aspartyl-isoleucine and valine, a composition comprising leucine, α-aspartyl-isoleucine and valine, a composition comprising leucine, isoleucine and α-aspartyl-valine, a composition comprising α-glutamyl-leucine, isoleucine and valine, a composition comprising α-glutamyl-leucine, α-glutamyl-isoleucine and valine, a composition comprising leucine, α-glutamyl-isoleucine and valine, and a composition comprising leucine, isoleucine and α-glutamyl-valine. More preferred examples include a composition comprising leucine, alanyl-isoleucine and valine, a composition comprising leucine, glycyl-isoleucine and valine, a composition comprising leucine, arginyl-isoleucine and valine, a composition comprising leucine, seryl-isoleucine and valine, a composition comprising leucine, α-aspartyl-isoleucine and valine, and a composition comprising leucine, α-glutamyl-isoleucine and valine.

The composition of the present invention may comprise other amino acid, if necessary. Examples of other amino acid include an aliphatic amino acid (specifically, glycine, alanine, etc.), hydroxyamino acid (specifically, serine, threonine, etc.), acidic amino acid (specifically, aspartic acid, glutamic acid, etc.), acidic amino acid amide (specifically, asparagine, glutamine, etc.), basic amino acid (specifically, lysine, hydroxylysine, arginine, ornithine, etc.), sulfur-comprising amino acid (specifically, cysteine, cystine, methionine, etc.), aromatic amino acid (specifically, phenylalanine, tyrosine, thyronine, etc.), heterocyclic amino acid (specifically, tryptophan, histidine, etc.) and imino acid (specifically, proline, 4-hydroxyproline, etc.).

In the composition of the present invention, the total leucine content is preferably 1 to 3 times the total valine content or the total isoleucine content, more preferably 1.5 to 2.5 times, and particularly preferably 1.6 to 2 times. Herein, the total leucine content denotes a sum of the content that is equivalent to leucine in a constituent amino acid of at least one dipeptide, which is selected from alanyl-leucine, glycyl-leucine, arginyl-leucine, seryl-leucine, α-aspartyl-leucine and α-glutamyl-leucine, and the content of leucine to be contained according to need. The total isoleucine content denotes a sum of the content that is equivalent to isoleucine in a constituent amino acid of at least one dipeptide, which is selected from alanyl-isoleucine, glycyl-isoleucine, arginyl-isoleucine, seryl-isoleucine, α-aspartyl-isoleucine and α-glutamyl-isoleucine, and the content of isoleucine to be contained according to need. The total valine content denotes a sum of the content that is equivalent to valine in a constituent amino acid of at least one dipeptide, which is selected from alanyl-valine, glycyl-valine, arginyl-valine, seryl-valine, α-aspartyl-valine and α-glutamyl-valine, and the content of valine to be contained according to need.

Although the composition of the present invention may take any forms, it is preferred to be a food or drug product. The food denotes a health food product such as a supplement, cooling beverage, nutritious supplement, nutritious functional food and specified health food, or a medical meal to be provided for the purpose of dietary cure for a patient. The drug product denotes an ethical drug, nonproperity drug and quasi-drug product.

Although the composition of the present invention is adaptable to an infusion and injection solution in the drug product, it is preferred to be a nutritious food or a drug product for oral administration. The nutritious food denotes the above-described food that is taken for the purpose of supplying nutritious components to patients such as valine, leucine and isoleucine. The drug product for oral administration denotes the above-described drug product that is taken for the purpose of oral intake of medicinal components such as valine, leucine and isoleucine. The form allowing oral use includes a tablet, granule and beverage.

In the present invention, the tablet denotes a conventional tablet, coated tablet, sustained-release tablet, intraorally rapidly disintegrable tablet, buccal tablet, chewable tablet, and the like, and the granule denotes a common granule, subtle granule, ball, powder, and the like. Incidentally, the granule includes a form by which the granule is dissolved in a liquid such as water upon using and administered to a human being, such as dry syrup.

In the present invention, the beverage denotes not only the above-described cooling beverage, but also all kind of drinking forms even if it belongs to other commodity classification. It denotes a liquid, syrup and elixir drug in the medical supply classification, while it denotes beverage which is synonymous with nutritious food in the medical meal classification.

In the present invention, the tablet or granule may contain, in addition to the dipeptide (1) and optionally the above amino acid as the principal active ingredients, a common diluent, disintegrant and the like used for common nutritious food or drug product. It may also comprise a binding agent, lubricant and other additives on request. The proportion of the principal active ingredients to the tablet or granule is preferably about 15 to 95% by mass, more preferably about 30 to 90% by mass, and most preferably about 60 to 80% by mass.

Examples of the diluent include saccharides (monosaccharides, disaccharides and polysaccharides) and sugar alcohol, and preferably include monosaccharides, disaccharides and sugar alcohols. The proportion of the diluent to the tablet or granule is preferably about 15 to 90% by mass, more preferably about 15 to 60% by mass, and most preferably about 20 to 40% by mass.

Examples of the monosaccharides or disaccharides include lactose, sucrose, maltose, trehalose, and the like. Examples of the sugar alcohol include mannitol, reduced malt sugar starch syrup, maltitol, maltol, lactitol, xylitol, sorbitol, erythritol, and the like. The monosaccharides, disaccharides or sugar alcohols can be optionally selected from one or, two or more kinds of combinations thereof, depending on the kind, the blended ratio, and the content of amino acid, and the like.

Preferred examples of the polysaccharides include as the diluent β-cyclodextrin, crystalline cellulose, and the like, and particularly β-cyclodextrin is preferred in the form of an intraorally rapidly disintegrable tablet.

Examples of the disintegrant include corn starch, potato starch, carboxymethyl cellulose, carboxymethyl cellulose calcium, carboxymethyl cellulose sodium, crospovidone, croscarmellose sodium, sodium carboxymethyl starch, and the like, and preferred examples include carboxymethylcellulose calcium and sodium carboxymethyl starch. The proportion of the disintegrant to the tablet or granule is preferably from 0.5 to 20% by mass, more preferably from 0.5 to 5% by mass, and most preferably from 0.5 to 2% by mass.

Examples of the binding agent include methylcellulose, ethylcellulose, carboxymethylcellulose, polyvinylpyrrolidone, pullulan, acrylic acid-based polymers, polyvinyl alcohol, gelatin, agar, acacia, powdered acacia, partially pregelatinized starch, macrogol, and the like. The proportion of the binding agent to the tablet or granule is preferably from 0.5 to 5% by mass, more preferably from 0.5 to 3% by mass, and most preferably from 0.5 to 2% by mass.

Examples of the lubricant include sucrose esters of fatty acid, magnesium stearate, calcium stearate, sodium stearyl fumarate, talc, sodium lauryl sulfate, light anhydrous silicic acid, hydrated silicon dioxide, sucrose fatty acid ester, and the like. The proportion of the lubricant to the tablet or granule is preferably from 0.05 to 10% by mass, more preferably from 0.1 to 5% by mass, and most preferably from 0.1 to 3% by mass.

Examples of other additives include colorants such as beta-carotene, food dye (such as Food Yellow No. 5, Food Red No. 2 and Food Blue No. 2), food lake dye, red ferric oxide, and niacin; vitamins such as vitamin E, ascorbic acid, vitamin Bs, vitamin A, vitamin D and derivatives thereof; minerals such as calcium, magnesium and sodium; sweeteners such as aspartame, glucose, fructose, sucralose, stevia, saccharose, saccharin sodium, thaumatin and acesulfame potassium; anticaking agents such as silicon dioxide, calcium silicate, synthetic aluminum silicate, talc and calcium hydrogenphosphate; foaming agents such as sodium bicarbonate; acidulants such as citric acid, malic acid and tartaric acid; and a flavor such as lemon, lemon lime, orange, grapefruit and menthol. Among these additives, one or, two or more kinds of these substances may be optionally used. The proportion of the additives to the tablet or granule is preferably from 0.01 to 5% by mass, more preferably from 0.1 to 3% by mass, and most preferably from 0.1 to 1% by mass.

The production method of the tablet may be either a direct tableting method or a wet method. In case of the direct tableting method, a composition for tableting, which comprises the dipeptide (1) and optionally the amino acid, diluent, disintegrant, binding agent, lubricant and/or other additives, is compressed as it is by a conventional method, while in case of an indirect tableting method, a tablet is produced as follows.

A composition including the dipeptide (1) and optionally the amino acid, diluent, disintegrant, binding agent, lubricant and/or other additives is charged in a granulator such as a stirring granulator, high speed stirring granulator, fluidized bed granulator, extrusion granulator and stirring fluidized bed granulator, preferably in a fluidized bed granulator. Granulation is performed in the usual manner as spraying water or water (binding water) comprising a diluent or a binding agent, preferably comprising at least one kind of methylcellulose, mannitol, erythritol, ethyl cellulose, carboxymethyl cellulose and pullulan, in an amount of 0.5 to 5% by mass, preferably from 1 to 4% by mass, and more preferably from 1.5 to 3.5% by mass, according to need. It is preferred to use water which is acceptable under the Food Sanitation Law or Pharmaceutical Affairs Law of Japan, such as purified water.

The resulted granule for tableting is then subjected to compression molding by an appropriate method to form a tablet. The compression molding method is not particularly limited, and a conventional known method can be applied. Example of the compression molding include a common method in which the amino acid, diluent, disintegrant, binding agent, lubricant and/or other additives are added on request to the granule for tableting, mixed and molded by compression, and a method in which the lubricant is applied on the surface of punch and on the die wall in advance, and the amino acid, diluent, disintegrant, binding agent and the like, except for the lubricant, are added on request to the granule for tableting, mixed and molded by compression.

Herein, the amino acid, diluent, disintegrant, binding agent, lubricant and other additives in the direct or indirect tableting method may take a powder or liquid form independently, or may take a granule form in which these agents are preliminary combined and granulated by a known wet or dry granulation method. Examples of the method for granulating the amino acid, diluent, disintegrant, binding agent, lubricant and/or other additives include a method of granulating them by adding water that is acceptable under the Food Sanitation Law or Pharmaceutical Affairs Law of Japan, such as purified water, to the above various additive components, and a method of granulating them by spraying water. Preferred examples thereof include the granulating method used in the production of the granule for tableting.

The hardness of the tablet of the present invention is preferably from 50 to 120 N, more preferably from 60 to 110 N, further preferably from 65 to 100 N, and most preferably from 70 to 90 N. A tablet softer than a common tablet is preferred when it is used as a chewable tablet. Incidentally, the hardness is measured in the diametral direction of the tablet, using a KHT-20N hardness tester (manufactured by Fujiwara Scientific Co., Ltd.) or the like.

The granule can be produced in the similar way as in the production method of the above granule for tableting, wherein the granule is pulverized and/or sieved according to need in each step so as to obtain an intended particle size.

When the amino acid is contained in the composition of the present invention, the amino acid is preferably used after being pulverized. The particle size of the amino acid to be used is preferably from 0.5 to 400 µm, more preferably from 5 to 200 µm, in terms of a volume average particle size measured by a microscopic or sieving method.

In the present invention, the beverage may contain, in addition to the dipeptide (1) and optionally the above amino acid as the principal active ingredients, auxiliary materials such as carbonated water, vitamins (synonymous with the above), an acidulant (synonymous with the above), a sweetener (synonymous with the above), a flavor (synonymous with the above), minerals (synonymous with the above), monosaccharides or disaccharides (synonymous with the above) and sugar alcohol (synonymous with the above). More preferably, it may comprise carbonated water, citric acid, ascorbic acid, sucrose, sucralose, aspartame, thaumatin, trehalose, erythritol, calcium, magnesium, sodium, and the like. The proportion of the principal active ingredients to the beverage is preferably about 15 to 95% by mass, more preferably about 30 to 90% by mass, and most preferably about 60 to 80% by mass, relative to the mass of the total solid matter, while it is preferably about 0.5 to 30% by mass, more preferably about 3 to 20% by mass, and most preferably about 10 to 15% by mass, relative to the mass of the solvent such as drinking water.

The beverage is prepared by adding water to a mixture of dipeptide (1) and optionally the amino acid and the auxiliary materials until concentration of the dipeptide (1) becomes the intended concentration, and adjusting the pH of the beverage with a pH adjusting agent, if necessary. Sterilization may also be allowed, if necessary, by high-temperature heating the mixture at 120° C. for 30 seconds to 30 minutes. In this case, the beverage may be sterilized first, and water may be added once again until the dipeptide (1) satisfies the necessary quantity.

Since the composition of the present invention is decomposed into valine, leucine or isoleucine in a body, it is used for alleviation of muscle fatigue, muscle building for enhancing athletic ability and reduction of body fat percentage, enhancing concentration, treatment of liver diseases, treatment of tardive dyskinesia and improvement of immune function which are the effect of valine, leucine or isoleucine. In addition, when the composition of the present invention is orally ingested or administered, it is superior to valine, leucine or isoleucine in terms of gustation, absorbability or nutritious and pharmacological effect. The intake or dosage cannot be generalized since it differs depending on purpose, gender, weight, age and others, but it is preferably from 0.1 to 20 g/day, more preferably about 1 to 10 g/day, and most preferably about 2 to 7 g/day, as a sum of the content which is equivalent to valine, leucine and isoleucine as the constituent amino acid in the dipeptide (1) and the content of at least one kind of the optionally contained amino acid selected from valine, leucine and isoleucine in the composition.

The present invention will now be described in detail by way of Examples, Reference Examples and Test Examples, but the present invention is not limited to the Examples.

Reference Example 1

400 mg of C-terminal His-tag addition type dipeptide synthetase collected by the method described in PATENT DOCUMENT 1, 33.1 g of $ATP_2Na$, 12.3 g of magnesium chloride, 2.7 g of L-alanine and 3.93 g of L-leucine were added to 1 L of a 100 mmol/L tris-HCl buffer solution (pH 8), and reaction was carried out at 37° C. for 16 hours. About 3.5 g of alanyl leucine was obtained.

Reference Example 2

400 mg of C-terminal His-tag addition type dipeptide synthetase collected by the method described in PATENT DOCUMENT 1, 33.1 g of $ATP_2Na$, 12.3 g of magnesium chloride, 2.7 g of L-alanine and 3.93 g of L-isoleucine were added to 1 L of a 100 mmol/L tris-HCl buffer solution (pH 8), and reaction was carried out at 37° C. for 16 hours. About 3.5 g of alanyl isoleucine was obtained.

Reference Example 3

400 mg of C-terminal His-tag addition type dipeptide synthetase collected by the method described in PATENT DOCUMENT 1, 33.1 g of $ATP_2Na$, 12.3 g of magnesium chloride, 2.7 g of L-alanine and 3.5 g of L-valine were added to 1 L of a 100 mmol/L tris-HCl buffer solution (pH 8), and reaction was carried out at 37° C. for 16 hours. About 3.1 g of alanyl valine was obtained.

Test Example 1

A male Wistar white rat (150±20 g) purchased from Japan SLC Inc., was adapted under fixed conditions (temperature: 24±2° C., humidity: 60±5%, light-dark cycle: 12 hours) for at least 3 days, and underwent abdominal opening surgery under anesthesia with Nembutal (Dainippon Sumitomo Pharma Co., Ltd.) to collect blood. To the blood collected, ethylenediamine tetraacetic acid (Nacalai Tesque, Inc.) and sodium citrate (Kishida Chemical Co., Ltd.) were added. The mixture was then subjected to centrifuge to obtain blood plasma.

Alanyl-valine (Kyowa Hakko Kogyo Co., Ltd.), alanyl-leucine (Kyowa Hakko Kogyo Co., Ltd.) or alanyl-isoleucine (Kyowa Hakko Kogyo Co., Ltd.) was dissolved in water to prepare a 10 mmol/L solution. 10 μL of the resultant dipeptide solution was mixed with 4 μL of blood plasma or 4 μL of water, and was incubated at 37° C. for 2 hours. The mixture solution after incubation was applied to a TLC plate (manufactured by Merck Ltd.), and developed with a solution containing butanol (Kishida Chemical Co., Ltd.), acetic acid (Kishida Chemical Co., Ltd.) and water in a ratio of 2:1:1. A 1% ninhydrin solution was sprayed onto the mixture, which was then incubated at 80° C. for 5 minutes. Incidentally, the 1% ninhydrin solution was prepared by dissolving ninhydrin (Wako Pure Chemical Industries, Ltd.) in ethanol (Kishida Chemical Co., Ltd.). The results are shown in Table 1.

When alanyl-valine, alanyl-leucine or alanyl-isoleucine was mixed with water, there was a single spot alone, whereas when alanyl-valine, alanyl-leucine or alanyl-isoleucine was mixed with the rat blood plasma, a spot by amino acid was further observed. According to the result, it was found that alanyl-valine, alanyl-leucine or alanyl-isoleucine was promptly decomposed into amino acids in the blood plasma.

TABLE 1

| Kind | + Water | + Blood Plasma |
| --- | --- | --- |
| Alanyl Valine | x | o |
| Alanyl Leucine | x | o |
| Alanyl Isoleucine | x | o | o BCAA is appeared
x BCAA is not appeared

Test Example 2

A taste sensory evaluation was performed by the panelists consisting of 3 males and 3 females, using alanyl-valine (Kyowa Hakko Kogyo Co., Ltd.), alanyl-leucine (Kyowa Hakko Kogyo Co., Ltd.), alanyl-isoleucine (Kyowa Hakko Kogyo Co., Ltd.), valine (Kyowa Hakko Kogyo Co., Ltd.), leucine (Kyowa Hakko Kogyo Co., Ltd.) or isoleucine (Kyowa Hakko Kogyo Co., Ltd.). The results are shown in Table 2. The kind of the test substance was blinded to the panelists. All of the 6 panelists responded that valine, leucine and isoleucine were "bitter", while alanyl-valine, alanyl-leucine and alanyl-isoleucine were "not bitter".

TABLE 2

| Kind | Sensory Awareness |
| --- | --- |
| Valine | x |
| Leucine | x |
| Isoleucine | x |
| Alanyl-Valine | o |
| Alanyl-Leucine | o |
| Alanyl-Isoleucine | o | x Taste bitter
o Do not taste bitter

Test Example 3

Alanyl-valine (Kyowa Hakko Kogyo Co., Ltd.), valine (Kyowa Hakko Kogyo Co., Ltd.), alanyl-isoleucine (Kyowa Hakko Kogyo Co., Ltd.) and isoleucine (Kyowa Hakko Kogyo Co., Ltd.) were respectively dissolved in a concentration of 200 mmol/L to water. Alanyl-leucine (Kyowa Hakko Kogyo Co., Ltd.) and leucine (Kyowa Hakko Kogyo Co., Ltd.) were respectively dissolved in a concentration of 133 mmol/L to water. A taste sensory evaluation comparing 2 solutions was performed by the panelists consisting of 3 males and 3 females between alanyl-valine (Kyowa Hakko Kogyo Co., Ltd.) and valine (Kyowa Hakko Kogyo Co., Ltd.), between alanyl-isoleucine (Kyowa Hakko Kogyo Co., Ltd.) and isoleucine (Kyowa Hakko Kogyo Co., Ltd.), and between alanyl-leucine (Kyowa Hakko Kogyo Co., Ltd.) and leucine (Kyowa Hakko Kogyo Co., Ltd.). The kind of the test substance was blinded to the panelists.

All of the 6 panelists responded that alanyl-valine, alanyl-leucine and alanyl-isoleucine were "not bitter" compared to valine, leucine and isoleucine.

Example 1

Alanyl-BCAA-Comprising Chewable Tablet

A mixture of 8 g of alanyl-valine (Kyowa Hakko Kogyo Co., Ltd.), 15 g of alanyl-leucine (Kyowa Hakko Kogyo Co., Ltd.), 7.5 g of alanyl-isoleucine (Kyowa Hakko Kogyo Co., Ltd.) and 70 g of maltitol (Towa Chemical Industry Co., Ltd., for foodstuff use, 50 mesh) was granulated with 8 mL of a 5% aqueous pullulan (Pullulan PF-20, Hayashibara Co., Ltd.) solution in a fluidized bed granulator (FL-MINI type, Freund Corporation). 0.8 g of magnesium stearate (San-Ei Gen F.F.I., Inc.) was added to the resultant granules (about 80 g), and the mixture was fully mixed in a polyethylene bag. A tablet of 8 mm in diameter and 240 mg in weight was produced using a single-punch tablet compression molding machine (Kikusui vertical molding machine 6B-2M, Kikusui Seisakusho Ltd.).

The resultant tablet was edible without hesitancy brought about by bitterness.

Example 2

Alanyl-Isoleucine-Comprising Chewable Tablet (Grapefruit Flavor)

A mixture of 67 g of maltitol (Towa Chemical Industry Co., Ltd., for foodstuff use, 50 mesh) and 25 g of alanyl-isoleucine (Kokusan Chemical Co., Ltd.) was granulated with 7 mL of a 5% aqueous pullulan (Pullulan PF-20, Hayashibara Co., Ltd.) solution in a fluidized bed granulator (FL-MINI type, Freund Corporation). 92 g of the resultant granule, 3 g of citric acid (Iwata Chemical Co., Ltd.), 1 g of aspartame (Ajinomoto Co., Inc.), 3 g of grapefruit flavor (SF Grapefruit JP, San-Ei Gen F.F.I., Inc.) and 1 g of silicon dioxide (Carplex, Shionogi & Co., Ltd.) were mixed. A tablet of 8 mm in diameter and 240 mg in weight was produced using a single-punch tablet compression molding machine (Kikusui vertical molding machine 6B-2M, Kikusui Seisakusho Ltd.).

Comparative Example 1

Isoleucine-Comprising Chewable Tablet (Grapefruit Flavor)

A mixture of 67 g of maltitol (Towa Chemical Industry Co., Ltd., for foodstuff use, 50 mesh), 16 g of isoleucine (Kyowa Hakko Kogyo Co. Ltd.) and 9 g of alanine (Kyowa Hakko Kogyo Co., Ltd.) was granulated with 7 mL of a 5% aqueous pullulan (Pullulan PF-20, Hayashibara Co., Ltd.) solution in a fluidized bed granulator (FL-MINI type, Freund Corporation). 92 g of the resultant granule, 3 g of citric acid (Iwata Chemical Co., Ltd.), 1 g of aspartame (Ajinomoto Co., Inc.), 3 g of grapefruit flavor (SF Grapefruit JP, San-Ei Gen F.F.I., Inc.) and 1 g of silicon dioxide (Carplex, Shionogi & Co., Ltd.) were mixed. A tablet of 8 mm in diameter and 240 mg in weight was produced using a single-punch tablet compression molding machine (Kikusui vertical molding machine 6B-2M, Kikusui Seisakusho Ltd.).

Test Example 4

A sensory evaluation was performed by the panelists consisting of 3 males and 3 females on the tablet produced in Example 2 (tablet A) and the tablet produced in Comparative Example 1 (tablet B). In a three point discrimination method, all of the 6 panelists discriminated the tablet A from the tablet B, and 5 panelists responded with the tablet A favorable. As the reason why the tablet B was not favorable, all of the 5 gave a "bitter taste".

Example 3

Alanyl-BCAA-Comprising Intraoral Rapidly Disintegrable Tablet

Alanyl-valine (Kokusan Chemical Co., Ltd.), alanyl leucine (Kokusan Chemical Co., Ltd.), alanyl-isoleucine (Kokusan Chemical Co., Ltd.), β-cyclodextrin (Seldex B-100, Nihon Shokuhin Kako Co., Ltd.), lactose (SUPER-TAB, Asahi Kasei Corp.), citric acid (Kyowa Hi Foods Co., Ltd.), calcium hydrogenphosphate (Taihei Chemical Industrial Co. Ltd.), orange flavor (T. Hasegawa Co., Ltd.) and sucralose (San-Ei Gen F.F.I., Inc.) were mixed in the compound content shown in Table 3, and fully mixed in a polyethylene bag. Sucrose fatty acid ester (DK Ester F20W, Dai-ichi Kogyo Seiyaku Co., Ltd.) was applied onto a punch and die as a lubricant, and a tablet of 15 mm in diameter and 750 mg in weight was produced using a single-punch tablet molding machine (Kikusui vertical molding machine 6B-2M, Kikusui Seisakusho Ltd.). The tableting pressure was adjusted, so as to be the tablet hardness of 5 kgf. Incidentally, the strength of the tablet was measured using a KHT-20N hardness tester (Fujiwara Scientific Co., Ltd.).

The tablet was intraorally disintegrated within one minute and did not make a bitter taste.

TABLE 3

| Composition | Compound Content A (wt %) |
|---|---|
| β-cyclodextrin | 60 |
| Lactose | 11.5 |
| Alanyl Valine | 6.5 |
| Alanyl Leucine | 12.3 |
| Alanyl Isoleucine | 6.2 |
| Citric Acid | 2 |
| Calcium Hydrogenphosphate | 1 |
| Orange Flavor | 0.45 |
| Sucralose (Sunsweet) | 0.05 |

Example 4

Alanyl-Leucine-Comprising Beverage 20 g of alanyl-leucine (Kokusan Chemical Co., Ltd.), 3 g of erythritol (Nikken Chemicals Co., Ltd.), 0.5 g of citric acid (Kyowa Hi Foods Co., Ltd.) and 0.01 g of sucralose (Sunsweet SA-8020, San-Ei Gen F.F.I., Inc.) were dissolved in 100 mL of water at 90° C. with stirring. The pH was adjusted to 3.3 with citric acid, and 0.1 g of orange flavor (San-Ei Gen F.F.I., Inc.) was added thereto so as to produce a beverage. It was heated at 90° C. for 15 minutes and allowed to stand. A clear beverage was obtained. The present beverage comprises alanyl leucine whose content is equivalent to 13 g of leucine in 100 mL thereof.

Comparative Example 2

Leucine-Comprising Beverage 3 g of leucine (Kyowa Hakko Kogyo Co., Ltd.), 3 g of erythritol (Nikken Chemicals Co., Ltd.), 0.5 g of citric acid (Kyowa Hi Foods Co., Ltd.) and 0.01 g of sucralose (Sunsweet SA-8020, San-Ei Gen F.F.I., Inc.) were added to 100 mL of water at 90° C. and stirred. Insoluble suspended solid and precipitate were observed, and a clear beverage was failed to produce. Even after adjusting the pH to 3.3 with citric acid, a clear beverage was not produced.

Example 5

Alanyl-BCAA-Comprising Powder for Cooling Beverage (No Vitamin, No Mineral)

Alanyl-valine (Kokusan Chemical Co., Ltd.), alanyl-leucine (Kokusan Chemical Co., Ltd.), alanyl-isoleucine (Kokusan Chemical Co., Ltd.), sucrose (granulated sugar, Nomura Co., Ltd.), citric acid (Kyowa Hi Foods Co., Ltd.), trehalose (Hayashibara Co., Ltd.), sucralose (Sunsweet SA-8020, San-Ei Gen F.F.I., Inc.), lemon flavor (Powdered Lemon 8318, Musashino Aromatic Chemical Laboratory) and ascorbic acid (Kahoku Yakuhin) were mixed in a plastic bag in the compound content shown in Table 4 (Example 5) to produce a powder for cooling beverage. When 15 g of the powder was dissolved in 50 mL of water, a clear beverage was obtained. In 50 mL of the beverage, valine, leucine and isoleucine were contained in an amount of 1.5 g, 3 g and 1.5 g, respectively.

TABLE 4

| Ingredient | Example 5 Compound Content % | Comparative Example 3 Compound Content % |
|---|---|---|
| Alanyl-Valine | 16 | — |
| Alanyl-Leucine | 31 | — |
| Alanyl-Isoleucine | 15 | — |
| Valine | — | 10 |
| Leucine | — | 20 |
| Isoleucine | — | 10 |
| Sucrose | 25.8 | 47.8 |
| Citric Acid | 5 | 5 |
| Trehalose | 5 | 5 |
| Sucralose (Sunsweet) | 1 | 1 |
| Lemon Flavor | 1 | 1 |
| Ascorbic Acid | 0.2 | 0.2 |

Comparative Example 3

BCAA-Comprising Powder for Cooling Beverage (No Vitamin, No Mineral)

Valine (Kyowa Hakko Kogyo Co., Ltd.), leucine (Kyowa Hakko Kogyo Co., Ltd.), isoleucine (Kyowa Hakko Kogyo Co., Ltd.), sucrose (granulated sugar, Nomura Co., Ltd.), citric acid (Kyowa Hi Foods Co., Ltd.), trehalose (Hayashibara Co., Ltd.), sucralose (Sunsweet SA-8020, San-Ei Gen F.F.I., Inc.), lemon flavor (Powdered Lemon 8318, Musashino Aromatic Chemical Laboratory) and ascorbic acid (Kahoku Yakuhin) were mixed in a plastic bag in the compound content shown in Table 4 (Comparative Example 3) to produce a powder for cooling beverage. When 15 g of the present powder was added to 50 mL of water, the powder did not dissolve therein and it was inadequate for drinking.

According to the result, it is clear that the composition of the present invention is excellent in solubility.

Example 6

Alanyl-BCAA-Comprising Powder for Cooling Beverage (with Vitamin and Mineral)

The powder for cooling beverage obtained in Example 5 was mixed with calcium lactate (Iwata chemical Co., Ltd.), magnesium oxide (Kyowa Hakko Kogyo Co., Ltd.), riboflavin (DSM Nutrition Japan K.K.), nicotinic acid amide (DSM Nutrition Japan K.K.), calcium pantothenate (San-Ei Gen F.F.I., Inc.), vitamin A (Dry Vitamin A, San-Ei Gen F.F.I., Inc.), pyridoxine hydrochloride (San-Ei Gen F.F.I., Inc.), thiamine hydrochloride (San-Ei Gen F.F.I., Inc.), vitamin D3 (Dry Vitamin D3, Nagase Biochemicals, Ltd.), vitamin B12 (0.1% Vitamin B12, DSM Nutrition Japan K.K.) and folic acid (DSM Nutrition Japan K.K.) in the compound content shown in Table 5 and a powder for cooling beverage was produced. 15 g of the present powder was dissolved in 50 mL of water, and a beverage was produced. The present beverage was favorably dosed.

TABLE 5

| Ingredient | Compound Content % |
|---|---|
| Powder for Cooling Beverage obtained in Example 5 | 99 |
| Calcium Lactate | 0.8 |
| Magnesium Oxide | 0.1 |
| Riboflavin | 0.03 |
| Nicotinic Acid Amide | 0.03 |
| Calcium Pantothenate | 0.01 |
| Vitamin A (Dry Vitamin A) | 0.01 |
| Pyridoxine Hydrochloride | 0.002 |
| Thiamine Hydrochloride | 0.005 |
| Vitamin D3 (Dry Vitamin D3) | 0.0005 |
| Vitamin B12 (0.1% Vitamin B12) | 0.003 |
| Folic Acid | 0.0003 |

Example 7

Glycyl-BCAA-Comprising Chewable Tablet

A mixture prepared by adding 3 mg of magnesium stearate (San-Ei Gen F.F.I., Inc.) to a mixture of 80 mg of glycyl-valine (Kokusan Chemical Co., Ltd.), 150 mg of glycyl-leucine (Kokusan Chemical Co., Ltd.), 75 mg of glycyl-isoleucine (Kokusan Chemical Co., Ltd.) and 2 g of maltitol (Towa Chemical Industry Co., Ltd., for foodstuff use, 50 mesh) was fully mixed in a polyethylene bag. A tablet of 8 mm in diameter and 240 mg in weight was produced using a single-punch tablet compression molding machine (Kikusui vertical molding machine 6B-2M, Kikusui Seisakusho Ltd.).

Example 8

Arginyl BCAA-Comprising Chewable Tablet

A mixture prepared by adding 3 mg of magnesium stearate (San-Ei Gen F.F.I., Inc.) to a mixture of 80 mg of arginyl-valine (Kokusan Chemical Co., Ltd., acetate), 150 mg of arginyl-leucine (Kokusan Chemical Co., Ltd., acetate), 75 mg of arginyl-isoleucine (Kokusan Chemical Co., Ltd., acetate) and 2 g of maltitol (Towa Chemical Industry Co., Ltd., for foodstuff use, 50 mesh) was fully mixed in a polyethylene bag. A tablet of 8 mm in diameter and 240 mg in weight was produced using a single-punch tablet compression molding machine (Kikusui vertical molding machine 6B-2M, Kikusui Seisakusho Ltd.).

Example 9

α-glutamyl-BCAA-Comprising Chewable Tablet

A mixture prepared by adding 3 mg of magnesium stearate (San-Ei Gen F.F.I., Inc.) to a mixture of 80 mg of α-glutamyl-valine (Kokusan Chemical Co., Ltd.), 150 mg of α-glutamyl-leucine (Senn Chemical), 35 mg of isoleucine (Kyowa Hakko Kogyo Co., Ltd.) and 2 g of maltitol (Towa Chemical Industry, for foodstuff use, 50 mesh) was fully mixed in a polyethylene bag. A tablet of 8 mm in diameter and 240 mg in weight was produced using a single-punch tablet compression molding machine (Kikusui vertical molding machine 6B-2M, Kikusui Seisakusho Ltd.).

Example 10

Alanyl-BCAA-Comprising Conventional Tablet

Alanyl-valine (Kokusan Chemical Co., Ltd.), alanyl-leucine (Kokusan Chemical Co., Ltd.), alanyl-isoleucine (Kokusan Chemical Co., Ltd.), reduced malt sugar starch syrup (Mabit 50 M, Hayashibara Co., Ltd.) and magnesium stearate (San-Ei Gen F.F.I., Inc.) were mixed in the compound content shown in Table 6, and fully mixed in a polyethylene bag. The resultant powder was subjected to direct compression molding, using a single-punch tablet molding machine (Kikusui vertical molding machine 6B-2M, Kikusui Seisakusho Ltd.), to prepare a tablet of 8 mm in diameter and 240 mg in weight. The tableting pressure was adjusted to 1.7 t. The hardness of the tablet was measured using a KHT-20N hardness tester (Fujiwara Scientific Co., Ltd.). No trouble was observed in the tableting procedure. A tablet of 12.7 kg in hardness was produced.

TABLE 6

| | Ingredient | Example 10 Compound Content % | Comparative Example 4 Compound Content % |
|---|---|---|---|
| Formulation | Alanyl-Valine | 16 | — |
| | Alanyl-Leucine | 31 | — |
| | Alanyl-Isoleucine | 15 | — |
| | Valine | — | 10 |
| | Leucine | — | 20 |
| | Isoleucine | — | 10 |
| | Reduced Malt Sugar Starch Syrup | 35 | 57 |
| | Magnesium Stearate | 3 | 3 |
| | Total | 100 | 100 |
| Tableting | Tableting Pressure | 1.7 t | 1.7 t |
| | Tablet Weight | 240 mg | 240 mg |
| | Tablet Hardness | 12.7 kgf | 5.5 kgf |

Comparative Example 4

BCAA-Comprising Conventional Tablet

Valine (Kyowa Hakko Kogyo Co., Ltd.), leucine (Kyowa Hakko Kogyo Co., Ltd.), isoleucine (Kyowa Hakko Kogyo Co., Ltd.), reduced malt sugar starch syrup (trade name: Mabit 50M, Hayashibara Co., Ltd.) and magnesium stearate (San-Ei Gen F.F.I., Inc.) were mixed in the compound content shown in Table 6, and fully mixed in a polyethylene bag. The content of valine, leucine and isoleucine in the present mixture was adjusted to be identical to those in Example 1. The resultant powder was subjected to direct compression molding, using a single-punch tablet molding machine (Kikusui vertical molding machine 6B-2M, Kikusui Seisakusho Ltd.), to prepare a tablet of 8 mm in diameter and 240 mg in weight. The tableting pressure was adjusted to 1.7 t. The strength of the tablet was measured using a KHT-20N hardness tester (Fujiwara Scientific Co., Ltd.). A capping tendency was observed in the tableting procedure. The hardness of the tablet was 5.5 kg on average, and there existed a tablet as fragile as being crumbled by hand.

It became apparent that the composition of the present invention is excellent in processing characteristics, such as tableting property.

INDUSTRIAL APPLICABILITY

The present invention provides a composition for oral administration which is excellent in nutrition, pharmacological effect and gustation and comprises at least one kind of dipeptide comprising valine, leucine or isoleucine. The present invention also provides a composition for oral administration which has improved solubility and tableting property by modifying at least one selected from valine, leucine and isoleucine into dipeptide, and comprises at least one kind of dipeptide comprising valine, leucine or isoleucine.

The invention claimed is:

1. A method comprising the step of orally administering to a human a composition, said composition comprising a comestible carrier and at least one dipeptide, wherein all dipeptides in said composition are represented by the formula:

wherein X is alanyl, and Y is selected from the group consisting of valine, leucine and isoleucine.

2. The method according to claim 1, wherein the composition is a nutritious food or a drug product.

3. The method according to claim 2, wherein the composition is a beverage.

4. The method according to claim 2, wherein the composition is a drug product comprising a pharmaceutically acceptable carrier.

5. The method according to claim 4, wherein the composition is a tablet or a granule.

6. The method according to claim 1, wherein the composition comprises three dipeptides wherein Y is each of valine, leucine and isoleucine, respectively.

7. The method according to claim 6, wherein the composition further comprises at least one kind of amino acid selected from the group consisting of valine, leucine and isoleucine.

8. The method according to claim 1, wherein the composition further comprises at least one amino acid selected from the group consisting of valine, leucine and isoleucine.

9. The method according to claim 6, wherein the total content of leucine in the composition is 1 to 3 times the total content of valine or total content of isoleucine.

10. The method according to claim 7, wherein the total content of leucine in the composition is 1 to 3 times the total content of valine or total content of isoleucine.

11. The method according to claim 8, wherein the total content of leucine in the composition is 1 to 3 times the total content of valine or total content of isoleucine.

12. The method according to claim 1, wherein Y is leucine, and the composition is a beverage.

13. The method according to claim 12, wherein the composition further comprises isoleucine.

14. The method according to claim 1, wherein the composition provides 0.1 to 20 g/day of the total amount of valine, leucine and isoleucine to said human.

15. The method according to claim 14, wherein the composition provides 1 to 10 g/day of the total amount of valine, leucine and isoleucine to said human.

16. The method according to claim 15, wherein the composition provides 2 to 7 g/day of the total amount of valine, leucine and isoleucine to said human.

17. The method according to claim 6, wherein the composition provides 0.1 to 20 g/day of the total amount of valine, leucine and isoleucine to said human.

18. The method according to claim 17 wherein the composition provides 1 to 10 g/day of the total amount of valine, leucine and isoleucine to said human.

19. The method according to claim 18, wherein the composition provides 2 to 7 g/day of the total amount of valine, leucine and isoleucine to said human.

* * * * *